(12) United States Patent
Chan

(10) Patent No.: US 7,861,348 B2
(45) Date of Patent: Jan. 4, 2011

(54) ELECTRIC TOOTHBRUSHES

(75) Inventor: John Geoffrey Chan, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1424 days.

(21) Appl. No.: 11/295,907

(22) Filed: Dec. 7, 2005

(65) Prior Publication Data

US 2006/0117505 A1 Jun. 8, 2006

Related U.S. Application Data

(60) Provisional application No. 60/634,142, filed on Dec. 8, 2004.

(51) Int. Cl.
*A46B 13/00* (2006.01)
*A47L 21/02* (2006.01)
*A47L 23/02* (2006.01)
*A47L 11/00* (2006.01)

(52) U.S. Cl. ............... 15/22.1; 15/22.2; 15/28

(58) Field of Classification Search ......... 15/22.1, 15/22.2, 28; 434/263
See application file for complete search history.

(56) References Cited

U.S. PATENT DOCUMENTS

| | | | |
|---|---|---|---|
| 164,353 A | 6/1875 | Wayne |
| 793,587 A | 6/1905 | Johnson |
| 800,422 A | 9/1905 | White |
| 1,212,001 A | 1/1917 | Baxter |
| 1,255,028 A | 1/1918 | Leonard et al. |
| 1,392,623 A | 10/1921 | Cheatham |
| 1,517,320 A | 12/1924 | Stoddart |
| 1,553,456 A | 9/1925 | Metrakos |
| 1,557,244 A | 10/1925 | Dominque |
| 1,896,731 A | 2/1933 | Lippett |
| 1,981,688 A | 11/1934 | Conti |
| 1,997,352 A | 4/1935 | Fleet |
| 2,044,863 A | 6/1936 | Sticht |
| 2,140,307 A | 12/1938 | Belaschk et al. |
| 2,172,624 A | 9/1939 | Robert |

(Continued)

FOREIGN PATENT DOCUMENTS

CN 2271352 7/1996

(Continued)

OTHER PUBLICATIONS

Bader, "Review of Currently Available Battery-Operated Toothbrushes", *Compend. Contin. Educ. Dent.*, vol. 13, No. 12, p. 1162, 1164-1169.

(Continued)

*Primary Examiner*—Joseph J Hail, III
*Assistant Examiner*—Jamal Daniel
(74) *Attorney, Agent, or Firm*—John P. Colbert; Vlad Witenberg; Richard Alexander

(57) ABSTRACT

An electric toothbrush is provided. The electric toothbrush has a handle, a head with carriers and a longitudinal axis, and a neck disposed between the handle and the head. A motor is disposed within the handle. A shaft is operatively connected to the motor. The shaft is operatively connected to the carrier to move the carrier in a first motion. The carrier is capable of moving in a second motion when subjected to user forces.

23 Claims, 8 Drawing Sheets

U.S. PATENT DOCUMENTS

| | | | |
|---|---|---|---|
| 2,215,031 A | 9/1940 | Elmore |
| 2,379,049 A | 6/1945 | Tompkins |
| 2,435,421 A | 2/1948 | Blair |
| 2,601,567 A | 6/1952 | Steinberg |
| 3,115,652 A | 12/1963 | Zerbee |
| 3,129,449 A | 4/1964 | Cyzer |
| 3,160,902 A | 12/1964 | Aymar |
| 3,178,754 A | 4/1965 | Cleverdon |
| 3,195,537 A | 7/1965 | Blasi |
| 3,242,516 A | 3/1966 | Cantor |
| 3,379,906 A | 4/1968 | Spohr |
| 3,398,421 A | 8/1968 | Rashbaum |
| 3,509,874 A | 5/1970 | Stillman |
| 3,524,088 A | 8/1970 | Ryckman |
| 3,538,530 A | 11/1970 | Stemme |
| 3,588,936 A | 6/1971 | Duve |
| 3,592,188 A | 7/1971 | Barnett |
| 3,935,869 A | 2/1976 | Reinsch |
| 3,945,076 A | 3/1976 | Sung |
| 3,978,852 A | 9/1976 | Annoni |
| 4,027,348 A | 6/1977 | Flowers et al. |
| 4,156,620 A | 5/1979 | Clemens |
| 4,175,299 A | 11/1979 | Teague, Jr. et al. |
| 4,274,173 A | 6/1981 | Cohen |
| 4,326,314 A | 4/1982 | Moret et al. |
| 4,346,492 A | 8/1982 | Solow |
| 4,397,055 A | 8/1983 | Cuchiara |
| 4,545,087 A | 10/1985 | Nahum |
| 4,791,945 A | 12/1988 | Moriyama |
| 4,795,347 A | 1/1989 | Maurer |
| 4,845,795 A | 7/1989 | Crawford |
| 4,974,278 A | 12/1990 | Hommann |
| 4,989,287 A | 2/1991 | Scherer |
| 4,995,131 A | 2/1991 | Takeda |
| 5,033,150 A | 7/1991 | Gross et al. |
| 5,068,939 A | 12/1991 | Holland |
| 5,070,567 A * | 12/1991 | Holland .......... 15/28 |
| 5,077,855 A | 1/1992 | Ambasz |
| 5,088,145 A | 2/1992 | Whitefield |
| 5,120,225 A | 6/1992 | Amit |
| 5,138,734 A | 8/1992 | Chung |
| 5,170,525 A | 12/1992 | Cataro |
| 5,186,627 A | 2/1993 | Amit et al. |
| 5,226,206 A | 7/1993 | Davidovitz et al. |
| 5,253,382 A | 10/1993 | Beny |
| 5,259,083 A | 11/1993 | Stansbury, Jr. |
| 5,276,932 A | 1/1994 | Byrd |
| 5,301,381 A | 4/1994 | Klupt |
| 5,311,633 A | 5/1994 | Herzog et al. |
| 5,353,460 A | 10/1994 | Bauman |
| 5,359,747 A | 11/1994 | Amakasu |
| 5,383,242 A | 1/1995 | Bigler et al. |
| 5,398,366 A | 3/1995 | Bradley |
| 5,404,608 A | 4/1995 | Hommann |
| 5,416,942 A | 5/1995 | Baldacci et al. |
| 5,448,792 A | 9/1995 | Wiedemann et al. |
| 5,465,444 A | 11/1995 | Bigler et al. |
| 5,493,747 A | 2/1996 | Inakagata et al. |
| 5,504,958 A | 4/1996 | Herzog |
| 5,504,959 A | 4/1996 | Yukawa et al. |
| 5,524,312 A | 6/1996 | Tan et al. |
| 5,528,786 A | 6/1996 | Porat et al. |
| 5,577,285 A | 11/1996 | Drossler |
| 5,617,601 A | 4/1997 | McDougall |
| 5,617,603 A | 4/1997 | Mei |
| 5,625,916 A | 5/1997 | McDougall |
| 5,679,991 A | 10/1997 | Wolf |
| 5,687,442 A | 11/1997 | McLain |
| 5,727,273 A | 3/1998 | Pai |
| 5,732,432 A | 3/1998 | Hui |
| 5,732,433 A | 3/1998 | Droessler et al. |
| 5,738,575 A | 4/1998 | Bock |
| 5,784,743 A | 7/1998 | Shek |
| RE35,941 E | 11/1998 | Stansbury, Jr. |
| 5,836,030 A | 11/1998 | Hazeu et al. |
| 5,842,244 A | 12/1998 | Hilfinger |
| 5,842,245 A | 12/1998 | Pai |
| 5,850,655 A | 12/1998 | Göcking et al. |
| 5,862,558 A | 1/1999 | Hilfinger et al. |
| 5,867,856 A | 2/1999 | Herzog |
| 5,956,797 A | 9/1999 | Wilson |
| 5,974,615 A | 11/1999 | Schwarz-Hartmann et al. |
| 6,000,083 A | 12/1999 | Blaustein et al. |
| 6,106,290 A | 8/2000 | Weissman |
| 6,138,310 A | 10/2000 | Porper et al. |
| 6,178,579 B1 | 1/2001 | Blaustein et al. |
| 6,189,693 B1 | 2/2001 | Blaustein et al. |
| 6,195,828 B1 | 3/2001 | Fritsch |
| 6,237,178 B1 | 5/2001 | Krammer et al. |
| 6,308,359 B2 | 10/2001 | Fritsch et al. |
| 6,311,837 B1 | 11/2001 | Blaustein et al. |
| 6,347,425 B1 | 2/2002 | Fattori et al. |
| 6,360,395 B2 | 3/2002 | Blaustein et al. |
| 6,371,294 B1 | 4/2002 | Blaustein et al. |
| 6,421,865 B1 | 7/2002 | McDougall |
| 6,421,866 B1 | 7/2002 | McDougall |
| 6,434,773 B1 | 8/2002 | Kuo |
| 6,446,294 B1 | 9/2002 | Specht |
| 6,449,792 B1 * | 9/2002 | Myers .......... 15/28 |
| 6,453,498 B1 | 9/2002 | Wu |
| 6,463,615 B1 | 10/2002 | Gruber et al. |
| 6,510,575 B2 | 1/2003 | Calabrese |
| 6,536,066 B2 | 3/2003 | Dickie |
| 6,546,585 B1 | 4/2003 | Blaustein et al. |
| 6,564,940 B2 | 5/2003 | Blaustein et al. |
| 6,574,820 B1 | 6/2003 | DePuydt et al. |
| 6,623,698 B2 | 9/2003 | Kuo |
| 6,725,490 B2 | 4/2004 | Blaustein et al. |
| 6,751,823 B2 | 6/2004 | Biro et al. |
| 6,760,946 B2 | 7/2004 | DePuydt |
| 6,836,917 B2 | 1/2005 | Blaustein et al. |
| 6,889,401 B2 | 5/2005 | Fattori et al. |
| 6,892,412 B2 | 5/2005 | Gatzemeyer et al. |
| 6,892,413 B2 | 5/2005 | Blaustein et al. |
| 6,928,685 B1 | 8/2005 | Blaustein et al. |
| 6,932,216 B2 | 8/2005 | Blaustein et al. |
| 6,944,901 B2 | 9/2005 | Gatzemeyer et al. |
| 6,952,854 B2 | 10/2005 | Blaustein et al. |
| 6,966,093 B2 | 11/2005 | Eliav et al. |
| 6,983,507 B2 | 1/2006 | McDougall |
| 7,124,461 B2 | 10/2006 | Blaustein et al. |
| 7,137,163 B2 | 11/2006 | Gatzemeyer et al. |
| 7,140,058 B2 | 11/2006 | Gatzemeyer et al. |
| 7,140,059 B2 | 11/2006 | Scherl |
| 7,150,061 B2 | 12/2006 | Kwong |
| 7,162,764 B2 | 1/2007 | Drossler et al. |
| 7,225,494 B2 | 6/2007 | Chan et al. |
| 7,258,747 B2 | 8/2007 | Vago et al. |
| 7,302,726 B2 | 12/2007 | Braun |
| 7,356,866 B2 | 4/2008 | Chan |
| 7,386,904 B2 | 6/2008 | Fattori |
| 7,392,562 B2 | 7/2008 | Boland et al. |
| 7,421,753 B2 | 9/2008 | Chan et al. |
| 7,430,777 B2 | 10/2008 | Scherl |
| 7,430,778 B2 | 10/2008 | Gatzemeyer et al. |
| 7,451,514 B2 | 11/2008 | Blaustein et al. |
| 7,520,016 B2 | 4/2009 | Kressner |
| 7,552,497 B2 | 6/2009 | Gatzemeyer et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0059685 A1 | 5/2002 | Paffrath |

| | | | | | | |
|---|---|---|---|---|---|---|
| 2002/0078514 | A1 | 6/2002 | Blaustein et al. | GB | 2290224 | 12/1995 |
| 2002/0138926 | A1 | 10/2002 | Brown, Jr. | GB | 2319170 | 5/1998 |
| 2002/0152564 | A1 | 10/2002 | Blaustein et al. | JP | 40-8743 | 8/1965 |
| 2002/0178519 | A1* | 12/2002 | Zarlengo .................... 15/22.2 | JP | 57-89810 | 6/1982 |
| 2003/0066145 | A1 | 4/2003 | Prineppi | JP | 2-19241 | 2/1990 |
| 2003/0074751 | A1 | 4/2003 | Wu | JP | 02-218309 | 8/1990 |
| 2003/0084524 | A1* | 5/2003 | Blaustein et al. ............. 15/22.1 | JP | 05-146313 | 6/1993 |
| 2003/0084525 | A1 | 5/2003 | Blaustein et al. | JP | 05-146314 | 6/1993 |
| 2003/0084526 | A1 | 5/2003 | Brown et al. | JP | 7-116020 | 5/1995 |
| 2003/0084527 | A1 | 5/2003 | Brown et al. | JP | 7-116021 | 5/1995 |
| 2003/0084528 | A1* | 5/2003 | Chan et al. .................. 15/22.1 | JP | 7-116023 | 5/1995 |
| 2003/0126698 | A1* | 7/2003 | Fritsch et al. ................ 15/22.1 | JP | 07-116024 | 5/1995 |
| 2003/0140435 | A1 | 7/2003 | Eliav et al. | JP | 7-93892 | 10/1995 |
| 2003/0140437 | A1 | 7/2003 | Eliav et al. | JP | 8-322641 | 10/1996 |
| 2003/0154567 | A1 | 8/2003 | Drossler et al. | JP | 2804940 | 7/1998 |
| 2003/0163881 | A1 | 9/2003 | Driesen et al. | KR | 1984-0004668 | 9/1984 |
| 2003/0163882 | A1 | 9/2003 | Blaustein et al. | KR | 1986-0001137 | 6/1986 |
| 2003/0182746 | A1 | 10/2003 | Fattori et al. | KR | 1994-0013418 | 7/1994 |
| 2003/0196283 | A1 | 10/2003 | Eliav et al. | KR | 1995-0002814 | 2/1995 |
| 2003/0213075 | A1 | 11/2003 | Hui et al. | KR | 1995-0010820 | 5/1995 |
| 2003/0226223 | A1 | 12/2003 | Chan et al. | KR | 1997-0000408 | 1/1997 |
| 2004/0045105 | A1 | 3/2004 | Eliav et al. | KR | 1997-0000409 | 1/1997 |
| 2004/0060137 | A1 | 4/2004 | Eliav et al. | KR | 1995-0024551 | 4/1998 |
| 2004/0074026 | A1 | 4/2004 | Blaustein et al. | KR | 143460 | 4/1998 |
| 2004/0083566 | A1 | 5/2004 | Blaustein | TW | 248031 | 12/1982 |
| 2004/0088807 | A1 | 5/2004 | Blaustein et al. | TW | 233472 | 5/1983 |
| 2004/0128780 | A1* | 7/2004 | Chan ......................... 15/22.1 | TW | 274724 | 4/1984 |
| 2004/0143917 | A1 | 7/2004 | Ek | TW | 256049 | 1/1993 |
| 2004/0168272 | A1 | 9/2004 | Prineppi | TW | 238504 | 6/1993 |
| 2004/0177458 | A1 | 9/2004 | Chan et al. | TW | 253174 | 7/1994 |
| 2004/0177462 | A1 | 9/2004 | Brown, Jr. | TW | 294031 | 11/1994 |
| 2005/0000043 | A1 | 1/2005 | Chan et al. | TW | 239964 | 2/1995 |
| 2005/0000045 | A1 | 1/2005 | Blaustein | TW | 309753 | 7/1997 |
| 2005/0091771 | A1 | 5/2005 | Blaustein et al. | TW | 330411 | 4/1998 |
| 2005/0102776 | A1 | 5/2005 | Mathur | TW | 406557 | 9/2000 |
| 2005/0155167 | A1 | 7/2005 | Gall | TW | 257968 | 7/2006 |
| 2005/0268625 | A1 | 12/2005 | Blaustein et al. | WO | WO 99/12492 | 3/1999 |
| 2005/0278874 | A1 | 12/2005 | Blaustein et al. | WO | WO 01/06946 | 2/2001 |
| 2006/0032006 | A1 | 2/2006 | Gall et al. | WO | WO 01/06947 | 2/2001 |
| 2006/0048314 | A1 | 3/2006 | Kressner | WO | WO 01/21094 | 3/2001 |
| 2006/0048315 | A1 | 3/2006 | Chan et al. | WO | WO 01/43586 | 6/2001 |
| 2006/0137118 | A1 | 6/2006 | Blaustein | WO | WO 02/102187 | 12/2002 |
| 2006/0254006 | A1 | 11/2006 | Blaustein et al. | WO | WO 03/020159 | 3/2003 |
| 2006/0254007 | A1 | 11/2006 | Banning | WO | WO 2004/045448 | 6/2004 |
| 2007/0251033 | A1 | 11/2007 | Gall et al. | | | |
| 2008/0010761 | A1 | 1/2008 | Blaustein et al. | | | |
| 2008/0016633 | A1 | 1/2008 | Blaustein et al. | | | |
| 2008/0078040 | A1 | 4/2008 | Braun | | | |
| 2009/0106923 | A1 | 4/2009 | Boland et al. | | | |

FOREIGN PATENT DOCUMENTS

| | | |
|---|---|---|
| CN | 2236827 Y | 10/1996 |
| CN | 2271353 | 10/1996 |
| CN | 2274947 Y | 2/1998 |
| CN | 1187341 A | 7/1998 |
| CN | 2324987 | 6/1999 |
| CN | 2324988 | 6/1999 |
| CN | 2681701 Y | 3/2005 |
| DE | 3406112 | 8/1985 |
| DE | 3544256 | 8/1987 |
| DE | 4003305 | 8/1991 |
| DE | 29600236 | 4/1996 |
| DE | 29613608 | 11/1996 |
| DE | 29618755 | 3/1997 |
| DE | 19701964 | 7/1998 |
| DE | 298 09 977 | 2/1999 |
| DE | 19802904 | 7/1999 |
| DE | 19803311 | 8/1999 |
| EP | 259648 | 3/1988 |
| EP | 1053721 | 11/2000 |
| EP | 1059049 | 12/2000 |
| GB | 2247297 | 2/1992 |

OTHER PUBLICATIONS

U.S. Appl. No. 10/237,902, filed Sep. 9, 2002 entitled Topper for Power Toothbrush and Method for Forming the Same, all pages.
Photographs of electric toothbrush of BioBrush Industries (22 photographs).
PCT International Search reports dated Jun. 2, 2003.
Office Action for U.S. Appl. No. 10/903,222; P&G Case 8777C; dated Apr. 11, 2005.
Office Action for U.S. Appl. No. 10/903,222; P&G Case 8777C; dated Oct. 19, 2004.
Office Action for U.S. Appl. No. 11/200,680; P&G Case 8777CC; dated Sep. 22, 2005.
Office Action for U.S. Appl. No. 11/358,582; P&G Case 8777CCC; dated Mar. 17, 2008.
Office Action for U.S. Appl. No. 11/358,582; P&G Case 8777CCC; dated Apr. 14, 2006.
Office Action for U.S. Appl. No. 11/358,582; P&G Case 8777CCC; dated Apr. 17, 2007.
Advisory Action for U.S. Appl. No. 11/358,582; P&G Case 8777CCC; dated Jun. 9, 2008.
Advisory Action for U.S. Appl. No. 11/358,582; P&G Case 8777CCC; dated Jul. 27, 2007.
Office Action for U.S. Appl. No. 11/358,582; P&G Case 8777CCC; dated Sep. 5, 2008.
Office Action for U.S. Appl. No. 11/358,582; P&G Case 8777CCC; dated Sep. 6, 2007.

Office Action for U.S. Appl. No. 11/358,582; P&G Case 8777CCC; dated Sep. 29, 2006.
Office Action for U.S. Appl. No. 10/676,955; P&G Case 8778CC; dated Jan. 24, 2005.
Office Action for U.S. Appl. No. 10/676,955; P&G Case 8778CC; dated Jul. 12, 2005.
Office Action for U.S. Appl. No. 10/676,955; P&G Case 8778CC; dated Jul. 29, 2004.
Office Action for U.S. Appl. No. 10/927,845; P&G Case 8778CCC2; dated Dec. 28, 2004.
Office Action for U.S. Appl. No. 10/929,288; P&G Case 8778CCC3; dated Mar. 18, 2005.
Office Action for U.S. Appl. No. 10/929,288; P&G Case 8778CCC3; dated Aug. 24, 2005.
Office Action for U.S. Appl. No. 11/514,742; P&G Case 8778CCC3C; dated Mar. 17, 2008.
Office Action for U.S. Appl. No. 11/514,742; P&G Case 8778CCC3C; dated Aug. 17, 2007.
Office Action for U.S. Appl. No. 11/514,742; P&G Case 8778CCC3C; dated Apr. 10, 2008.
Office Action for U.S. Appl. No. 11/006,972; P&G Case 8778CCC4; dated Mar. 24, 2004.
Office Action for U.S. Appl. No. 10/896,540; P&G Case 8778CCC; dated Oct. 4, 2004.
Office Action for U.S. Appl. No. 11/414,908; P&G Case 8829RRCC; dated May 23, 2007.
Office Action for U.S. Appl. No. 10/308,959; P&G Case 8880R; dated Feb. 16, 2006.
Advisory Action for U.S. Appl. No. 11/486,725; P&G Case 8880RC; dated Jan. 28, 2008.
Office Action for U.S. Appl. No. 11/486,725; P&G Case 8880RC; dated Jan. 28, 2009.
Office Action for U.S. Appl. No. 11/486,725; P&G Case 8880RC; dated Jan. 29, 2007.
Office Action for U.S. Appl. No. 11/486,725; P&G Case 8880RC; dated Apr. 10, 2008.
Office Action for U.S. Appl. No. 11/486,725; P&G Case 8880RC; dated Aug. 13, 2007.
Office Action for U.S. Appl. No. 11/893,469; P&G Case 8880RCC; dated Oct. 14, 2008.
Office Action for U.S. Appl. No. 11/893,469; P&G Case 8880RCC; dated Dec. 18, 2008.
Office Action for U.S. Appl. No. 11/410,808; P&G Case 9186C; dated Feb. 15, 2007.
Office Action for U.S. Appl. No. 11/410,808; P&G Case 9186C; dated Jul. 17, 2007.
Office Action for U.S. Appl. No. 11/015,111; P&G Case 9487; dated Nov. 24, 2008.
Office Action for U.S. Appl. No. 11/220,219; P&G Case 9770; dated Oct. 20, 2008.
Office Action for U.S. Appl. No. 10/367,373; dated Mar. 9, 2004.
Office Action for U.S. Appl. No. 09/425,423; P&G Case Z-3735; dated Jan. 31, 2002.
Office Action for U.S. Appl. No. 09/425,423; P&G Case Z-3735; dated Aug. 14, 2002.
Office Action for U.S. Appl. No. 10/331,799; P&G Case Z-3557; dated Apr. 19, 2005.
Office Action for U.S. Appl. No. 10/331,799; P&G Case Z-3557; dated Oct. 14, 2005.
Office Action for U.S. Appl. No. 10/331,799; P&G Case Z-3557; dated Feb. 23, 2006.
Office Action for U.S. Appl. No. 09/993,167; P&G Case 8778; dated Dec. 18, 2002.
Office Action for U.S. Appl. No. 09/993,167; P&G Case 8778; dated Apr. 16, 2003.
International Search Report PCT/US2005/044604; dated Apr. 27, 2006.

* cited by examiner

ELECTRIC TOOTHBRUSHES

CROSS REFERENCE TO RELATED APPLICATION

This application claims the benefit of U.S. Provisional Application No. 60/634,142 filed on Dec. 8, 2004, the substance of which is incorporated herein by reference.

TECHNICAL FIELD OF THE INVENTION

The present invention relates to electric toothbrushes, and, more particularly, to toothbrushes having carriers which have move in multiple motions.

BACKGROUND OF THE INVENTION

Electric toothbrushes utilizing moving carriers are known in the art. However, there is a continuing desire to provide electric toothbrushes utilizing carriers that have multiple motions, which are mechanically efficient, and/or which can provide smaller more compact arrangements.

SUMMARY OF THE INVENTION

An electric toothbrush is provided. The electric toothbrush may have a handle, a head with a carrier and a longitudinal axis, and a neck disposed between the handle and the head. A motor may be disposed within the handle. A shaft may be operatively connected to the motor. The shaft may be operatively connected to the carrier to move the carrier in a first motion. The carrier may move in a second motion when subjected to user forces.

BRIEF DESCRIPTION OF THE DRAWINGS

While the specification concludes with claims directed to the invention, it is believed that the present invention will be better understood from the following description taken in conjunction with the accompanying drawings in which:

DETAILED DESCRIPTION OF THE INVENTION

Figure 1:
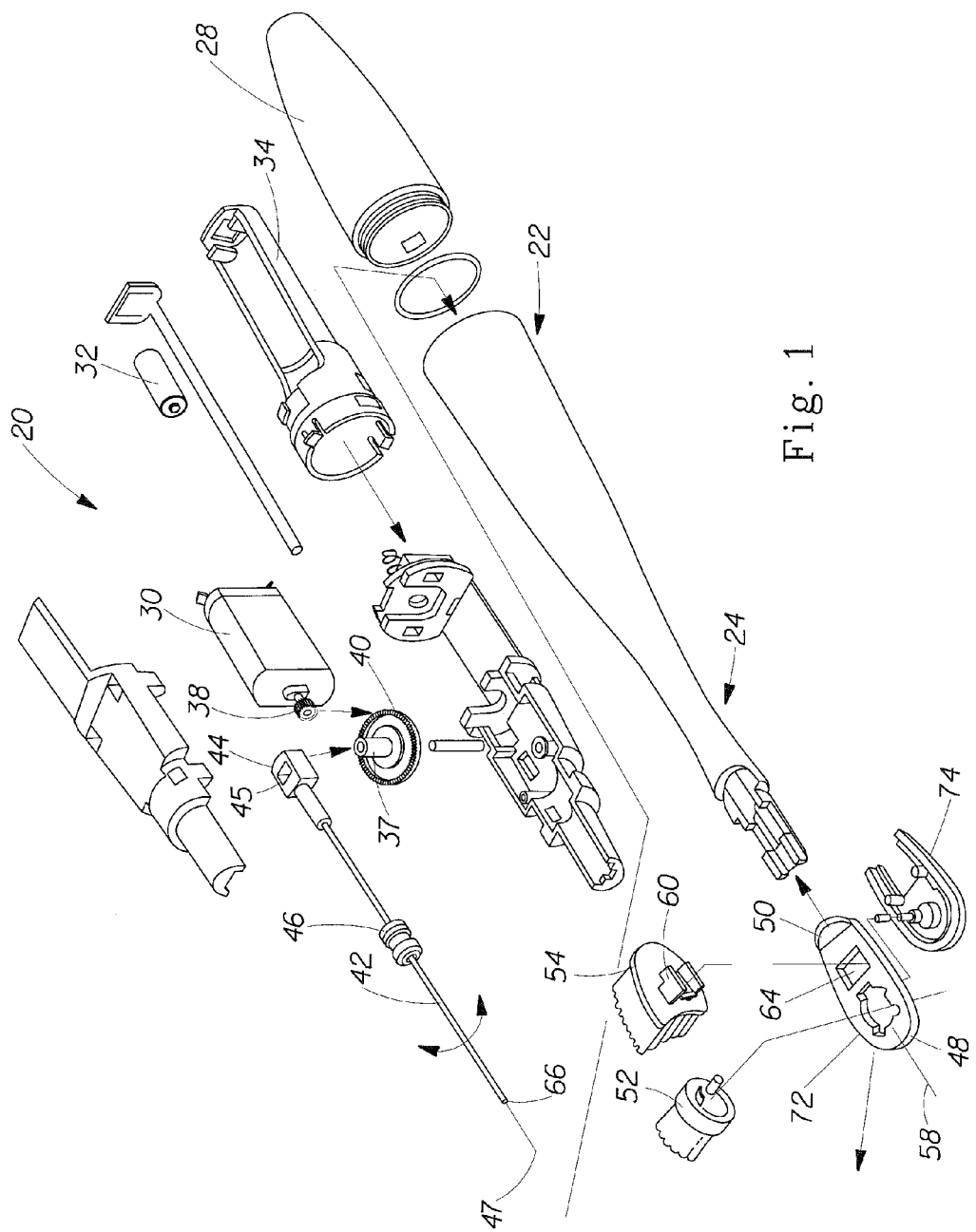
FIG. 1 is an exploded perspective view of an electric toothbrush made in accordance with the present invention.
Figure 2:
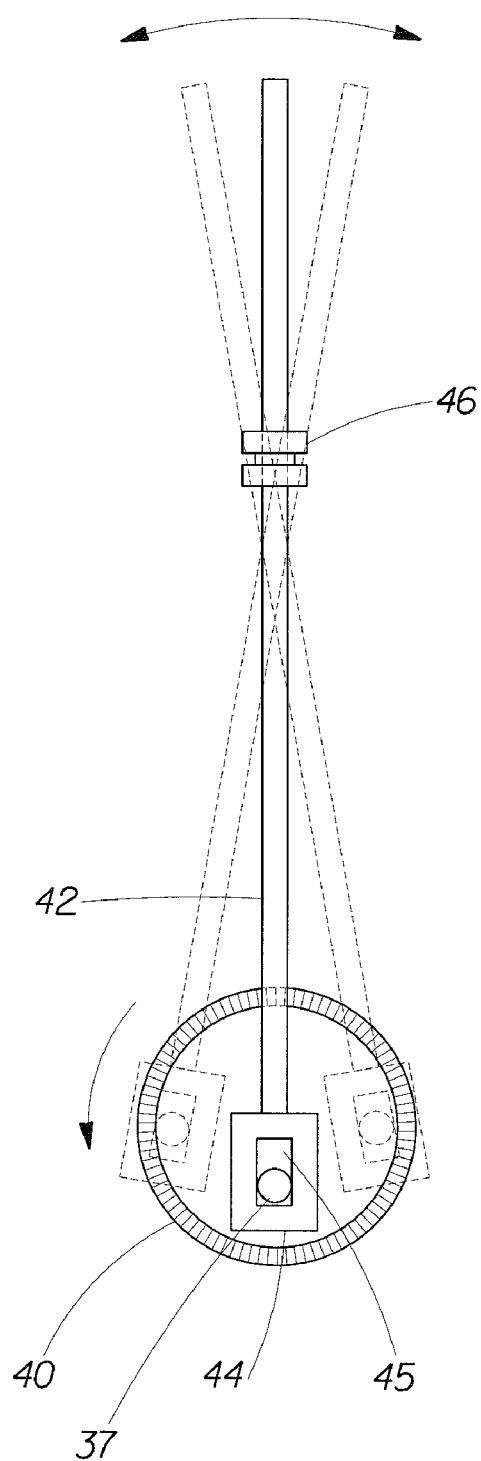
FIG. 2 is a top plan view of the shaft, bushing, and driven gear of the electric toothbrush of FIG. 1.

Reference will now be made to various embodiments of the present invention, examples of which are illustrated in the accompanying drawings wherein like numerals indicate the same elements throughout the views. Referring to FIG. 1, an electric toothbrush 20 will now be described. The electric toothbrush 20 may comprise a handle 22, a neck 24, and a head 26. The neck 24 may be integrally formed with the handle 22 or may be provided as a separate component. The handle 22 may have a cap 28 that threadably engages a portion of the handle 22. An electric motor 30 may be disposed within the handle 22 along with a voltage source. The voltage source may be provided in the form of one or more batteries 32 which may be received in a cradle 34 that may be disposed within the handle 22. The motor 30 may have a rotatable output shaft and an output gear 38 attached to the rotatable output shaft. The output gear 38 may engage a driven gear 40 which in turn may be operatively connected to a shaft 42 having a coupling 44 with an elongated slot 45 that may engage an eccentric post 37 of the driven gear 40. The slot 45 may be aligned along the longitudinal axis 47 of the shaft 42. The shaft may include a bushing 46 that may be captured by the handle 22 or neck 24. The bushing 46 may be formed of any flexible material that allows the shaft 42 to pivot about the bushing 46. Suitable materials can include elastomeric polymers, such as natural or synthetic rubbers. The bushing 46 may act as a pivot about which the shaft 42 moves. The location of the bushing 46 may be varied along the length of the shaft 42 in order to achieve a desired amount of side-to-side motion at the end of the shaft 42 adjacent the head 26. As the driven gear 40 rotates, the shaft 42 may pivot about the bushing 46 in a side-to-side motion (see FIG. 2). The side-to-side motion of the shaft 42 may occur substantially or entirely in a single plane.

Figure 4:
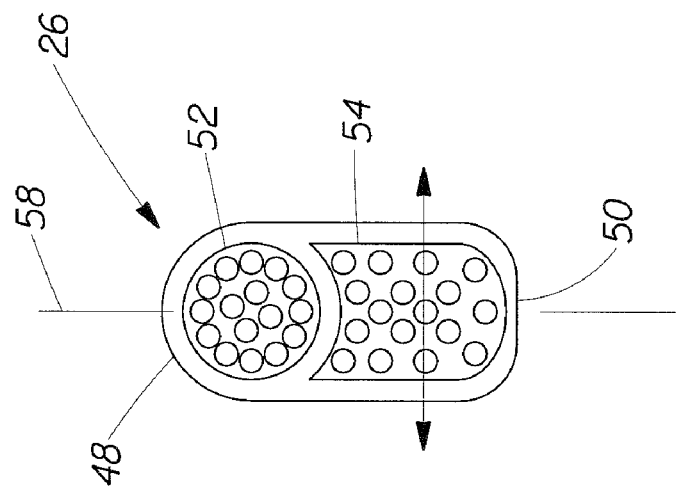
FIG. 4 is a top plan view of the head of FIG. 3.
Figure 3:
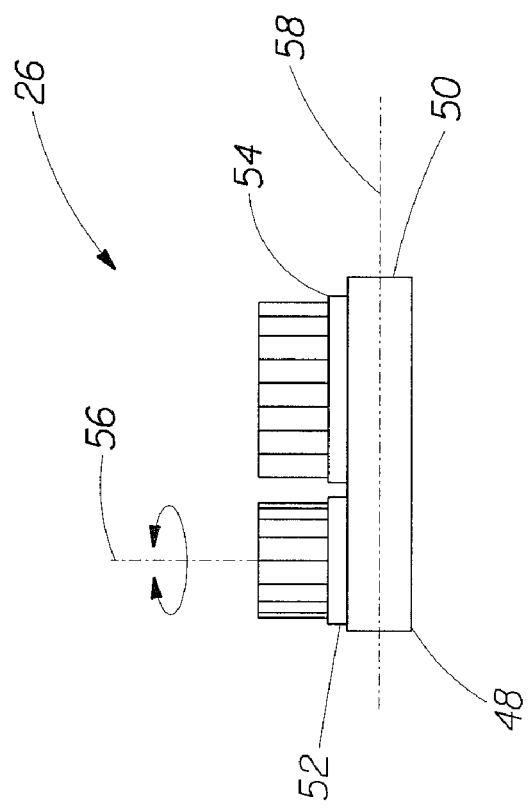
FIG. 3 is a side elevation view of the head of the toothbrush of FIG. 1.
Figure 5:
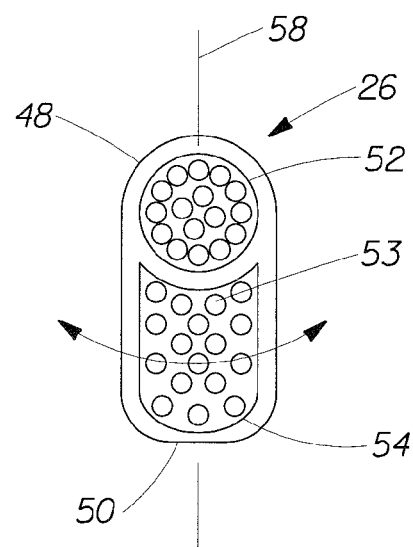
FIG. 5 is a top plan view of another embodiment of a head suitable for use with the toothbrush of FIG. 1.

Further as shown in FIG. 1, the head 26 may be made up of a top housing 70 (see FIG. 8), a middle housing 72, and a bottom housing 74. The head 26 may have a first free end 48 and a second end 50 that engages the neck 24. The head may include one or more carriers. The electric toothbrush 20 may comprise one or multiple carriers. A first carrier 52 may be disposed adjacent the first end 48 and a second carrier 54 may be disposed adjacent the second end 50. As shown in FIG. 3, the first carrier may oscillate about an axis 56 that is substantially perpendicular to a longitudinal axis 58 of the head 26. A shown in FIG. 4, the second carrier 54 may reciprocate in a side-to-side direction or motion perpendicular to the longitudinal axis 58 of the head 26. While the side-to-side motion shown in FIG. 4 may be substantially perpendicular to the longitudinal axis 58 of the head 26, it is contemplated that other side-to-side motions of the second carrier 54 can be provided. For example, the second carrier 54 might swing or pivot about a pin or hinge 53. As shown in FIG. 5, the pin or hinge 53 could be provided at other locations on the second carrier 54, such as at either end or in the middle to provide different types of side-to-side motions.

Figure 6:
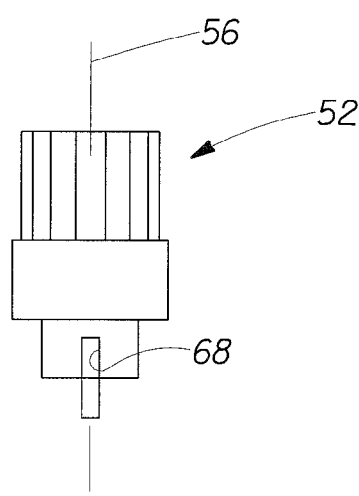
FIG. 6 is a side elevational view of the first carrier of the toothbrush of FIG. 1.
Figure 7:
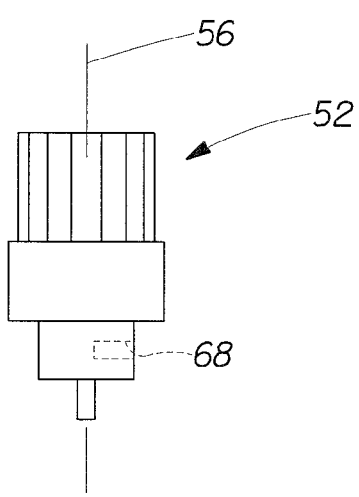
FIG. 7 is another side elevational view of the first carrier of FIG. 6.
Figure 8:
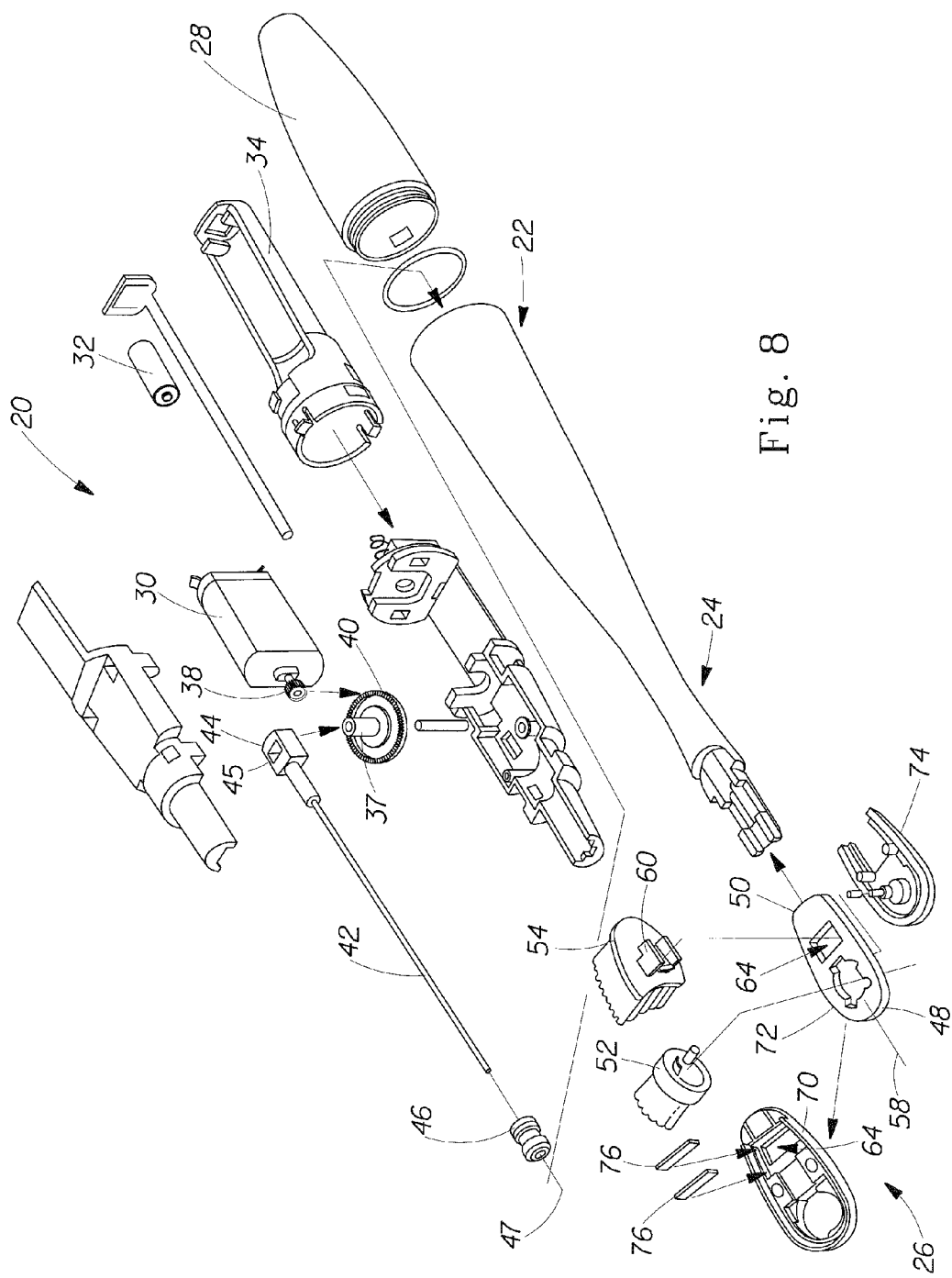
FIG. 8 is an exploded perspective view of an alternate embodiment of FIG. 1, illustrating the head with flexible walls.

As shown in FIGS. 6 and 7, the end 66 of the shaft 42 may operatively engage a slot 68 of the first carrier 52 to move the first carrier 52 in an oscillating motion about the axis 56. As shown in FIG. 8, the shaft 42 may pass through cam followers 60 of the second carrier 54. The cam followers 60 may receive a portion of the shaft 42. The cam followers 60 may be received in the slot 64 of the head 26, such that the slot 64 generally guides the second carrier 54 in its side-to-side motion.

Figure 9:
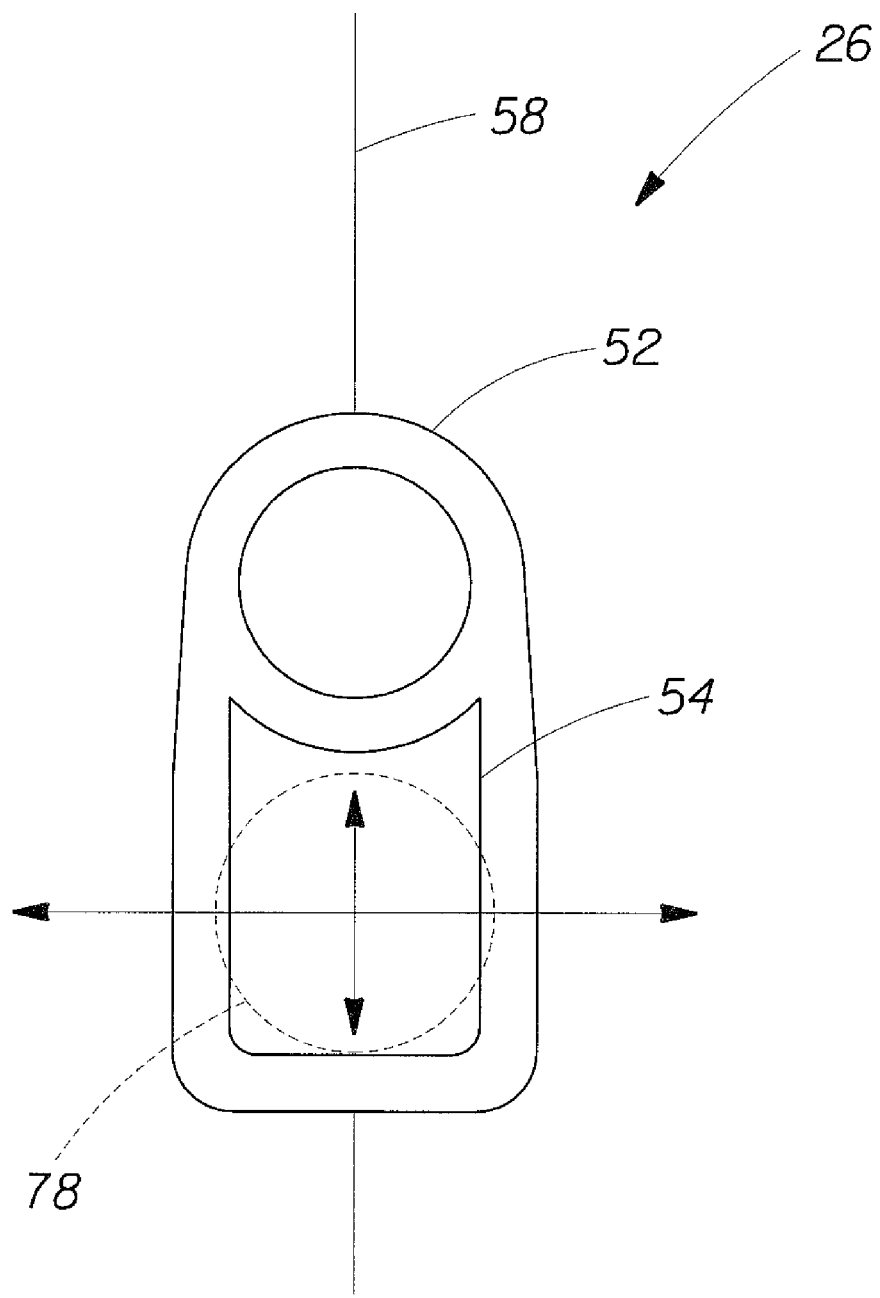
FIG. 9 is a top view of the head of FIG. 8.

A portion of the slot 64 may be flanked by flexible walls 76. The flexible walls 76 may be oriented transverse to the longitudinal axis 58 of the head 26. The flexible walls 76 may allow for movement of the second carrier 54 in a motion along the longitudinal axis 58 of the head 26 when the second carrier 54 is subjected to user forces. That is, when a user turns the toothbrush 20 on, the second carrier 54 may only move from side-to-side. However, when the user brushes her teeth, she will likely introduce forces which manipulate the second carrier 54 in directions and motions beyond the side-to-side motion. These forces will likely include ones which move the second carrier 54 generally along the longitudinal axis 58 of the head 26. The flexible walls 76 will allow the second carrier 54, to a degree, to travel along the longitudinal axis 58 of the head 26 (see FIG. 9). The motion of the second carrier 54 when manipulated by the user may be in the motion of an oval 78, a circle, etc., as such is consistent with standard brushing motions. When the second carrier 54 is not confined to a first motion (e.g., side-to-side relative to the longitudinal axis of the head), the battery power of the brush is normally preserved because the manipulative or biasing forces of the user when brushing or flossing her teeth are transferred into a second motion (e.g., along or in-line with the longitudinal axis of the head) instead of working against the first motion. Simply put, user forces which once worked against the first motion are now used to create a second, third, fourth, etc. motion.

The flexible walls 76 may not bias the second carrier 54 until user forces move the second carrier 54 against the flexible walls 76. This may be accomplished by orienting the flexible walls 76 immediately adjacent the second carrier 54, such that there is no room for the second carrier to float between the flexible walls. Also, a desired amount of space between the second carrier 54 and the flexible walls 76 may be left. Further, it may be desirable to use a single flexible wall 76, providing a more limited pathway for the second carrier 54 to travel upon when subjected to user forces.

It is also contemplated that the cam followers 60 may be fully surrounded by flexible walls 76, such that even the first motion of the second carrier 54 may be complemented by user forces, such that the side-to-side motion of the second carrier 54 may be widened by user forces.

Rather than making a part of the structure of the housings (e.g., 70, 72, and 74) of the head 26 flexible, like dynamics may be realized by making at least a portion of the cam follower 60 flexible. The cam follower 60 may comprise suitable materials including elastomeric polymers, such as natural or synthetic rubbers.

Figure 10:
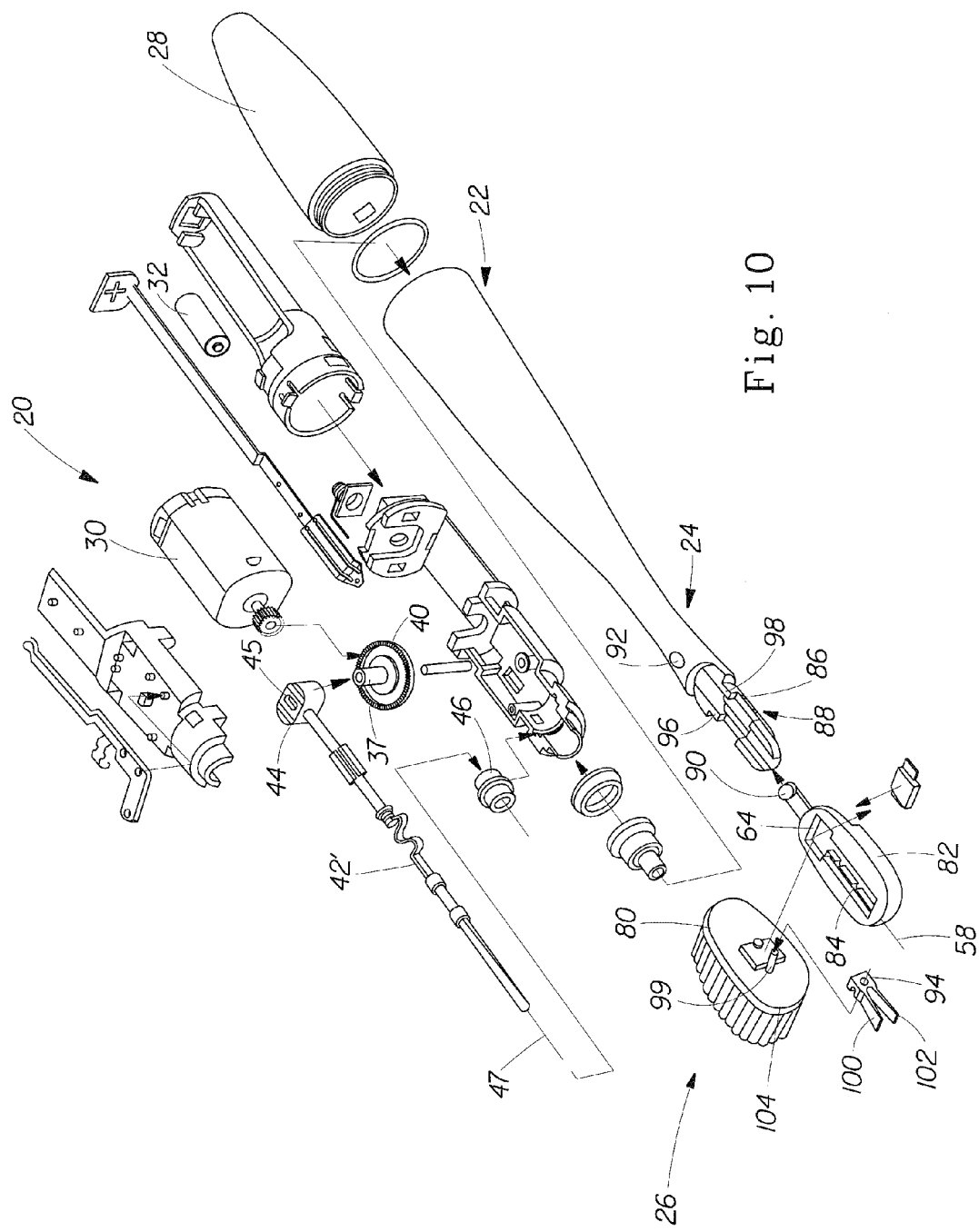
FIG. 10 is an exploded perspective view of an alternate embodiment of FIG. 1, illustrating the head with a spring clip.

As shown in FIG. 10, the electric toothbrush 20 may comprise only a single carrier 80 which reciprocates along the longitudinal axis 58 of the head 26. The head 26 may comprise a main housing 82 having an elongated slot 64 running along its longitudinal axis 58. The slot 64 may have grooves 84 which receive tabs 86 of the receiving end 88 of the neck 24. The main housing 82 may also have a ball joint 90 which is received in an opening 92 of the neck 24. The carrier 80 may have an arm 99 which is fixed or operably connected to a spring clip 94.

The carrier 80 may be reciprocated along the elongated slot 64 by the shaft 42', and thus along or in-line with the longitudinal axis 58 of the head 26. As the carrier 80 moves in a motion along the elongated slot 64, the spring clip 64 may ride along a left side wall 96 and a right side wall 98 of the neck 24 such that a left leg 100 and a right leg 102 of the spring clip 94 is biased against the left side wall 96 and right side wall 98. Alternatively, the spring clip 94 may float between the right and left sidewalls 96 and 98.

Figure 12:
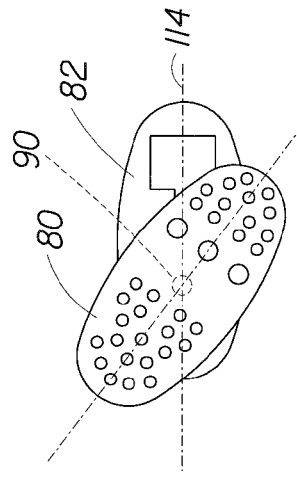
FIG. 12 is a top view of the head of FIG. 10.
Figure 11:
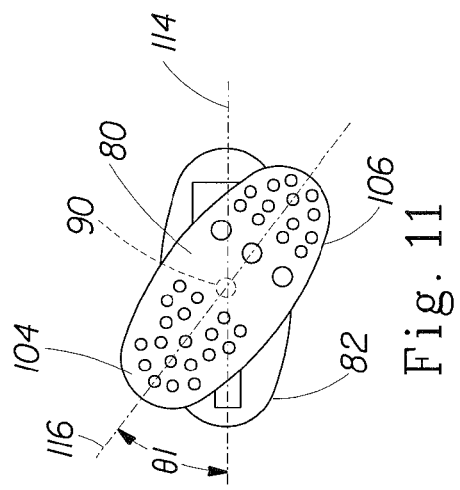
FIG. 11 is a top view of the head of FIG. 10.

The spring clip 94 may allow for movement of the carrier 80 in a motion transverse to the longitudinal axis 58 of the head 26 when the carrier 80 is subjected to user forces. That is, when a user turns the toothbrush 20 on, the carrier 80 may only move along the longitudinal axis 58 of the head 26. However, when the user brushes her teeth, likely manipulating the motion of the carrier 80 generally transverse to the longitudinal axis 58 of the head 26, the spring clip 94 may allow the carrier 80, to a degree, to travel transverse to the longitudinal axis 58 of the head 26. Thus, as the carrier 80 is moving along the longitudinal axis 58 of the head 26, it may also be moved transverse to the longitudinal axis 58 of the head 26. As the carrier 80 is subjected to user forces it may be pivoted around the arm 90. Thus, as shown in FIGS. 11 and 12, as a front portion 104 of the carrier 80 is moved transverse to the longitudinal axis 58 of the head 26 in one direction, a back portion 106 of the carrier 80 is moved transverse to the longitudinal axis 58 of the head 26 in the opposite direction. The carrier 80 may be pivoted such that a longitudinal axis 116 of the carrier 80 is from about 5 to about 50 degrees, from about 15 to about 30 degrees, or from about 20 to about 25 degrees from a longitudinal axis 114 of the main housing 82 ($\theta$1), whereas when the carrier 80 is not pivoted, its longitudinal axis 116 is generally in-line with the longitudinal axis 114 of the main housing 82, and thus generally in-line with the longitudinal axis 47 of the shaft 42'.

The spring clip 94 may bias the carrier 80 only slightly when no user forces are present, and more greatly once the carrier 80 encounters user forces. Alternatively, when no user forces are present, the spring clip 94 may float between the sidewalls 96 and 98 of the neck 24, such that the spring clip 94 does not bias the carrier 80 until user forces are present, forcing the spring clip 94 against a sidewall 96 or 98 of the neck 24, and thus biasing the carrier 80.

Figure 14:
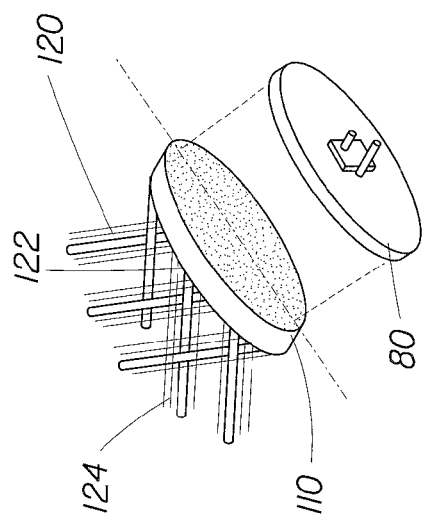
FIG. 14 is an exploded perspective view of the head of FIG. 10 comprising an attachable/detachable bristle plate.
Figure 13:
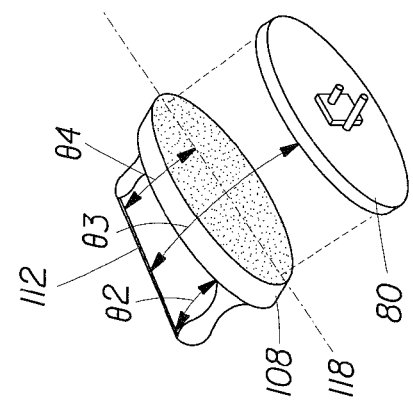
FIG. 13 is an exploded perspective view of the head of FIG. 10 comprising an attachable/detachable floss plate.

As shown in FIGS. 13 and 14, the carrier 80 may receive attachable/detachable bristle plates 108 or attachable/detachable floss plates 110. The plates 108 and 110 may be attached by hook and loop, snap-fit, friction-fit, threads (on circular plates), etc. Further, the floss 112 may be oriented at an angle from about 5 to about 50 degrees, from about 15 to about 30 degrees, or from about 20 to about 25 degrees relative to a top surface of the base of the plate 108 ($\ominus$2), or a top surface of the carrier 80 ($\ominus$3), or a longitudinal axis 118 of the floss plate 108 ($\ominus$4).

The bristles 120 may be angled relative to a top surface 122 of the bristle plate 110. One or more of the bristles 120 or tufts of bristles may be made of natural or synthetic elastomeric materials. The bristle plate 110 may also comprise one or more elastomeric fingers 124.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
   a handle;
   a head comprising a carrier and a longitudinal axis;
   a neck disposed between said handle and said head;
   a motor disposed within said handle; and
   a shaft operatively connected to said motor, wherein said shaft is operatively connected to said carrier to move said carrier in a first motion, and wherein said carrier is capable of moving in a second motion when subjected to user forces, said head further comprising a spring in operative communication with said carrier, wherein said spring biases said carrier when said carrier moves in said first motion and biases said carrier when said carrier moves in said second motion, and wherein said spring's bias upon said carrier is greater during said second motion than said first motion, wherein said spring is one or more flexible walls.

2. The electric toothbrush of claim 1, wherein said spring does not substantially bias said carrier when said carrier moves in said first motion, and wherein said spring does bias said carrier when said carrier moves in said second motion.

3. The electric toothbrush of claim 2, wherein said first motion is generally transverse to said longitudinal axis of said head.

4. The electric toothbrush of claim 3, wherein said carrier supports an attachable/detachable bristle plate or an attachable/detachable flossing plate.

5. The electric toothbrush of claim 4, wherein said bristle plate comprises at least one bristle tuft that forms an acute angle with a top surface of said bristle plate.

6. The electric toothbrush of claim 5, wherein said head comprises a second carrier which oscillates about an axis transverse to said longitudinal axis of said head.

7. The electric toothbrush of claim 6, wherein said second carrier comprises an elastomeric finger.

8. The electric toothbrush of claim 3, wherein said second motion is generally along said longitudinal axis of said head.

9. The electric toothbrush of claim 1, wherein said first motion is generally along said longitudinal axis of said head.

10. The electric toothbrush of claim 9, wherein said carrier supports an attachable/detachable bristle plate or an attachable/detachable flossing plate.

11. The electric toothbrush of claim 10, wherein said flossing plate comprises floss, and wherein said floss is oriented from about 30 to about 45 degrees relative to a longitudinal axis of said carrier.

12. The electric toothbrush of claim 11, wherein said head comprises a second carrier which oscillates about an axis transverse to said longitudinal axis of said head.

13. The electric toothbrush of claim 9, wherein said second motion is generally transverse to said longitudinal axis of said head.

14. The electric toothbrush of claim 1, wherein said flexible walls are arranged to allow for said first motion to be complemented by user forces.

15. The electric toothbrush of claim 1, wherein said carrier comprises a flexible cam which allows for said first or second motions to be complemented by user forces.

16. An electric toothbrush, comprising:
    a handle;
    a head comprising a carrier and a longitudinal axis;
    a neck disposed between said handle and said head;
    a motor disposed within said handle; and
    a shaft operatively connected to said motor, wherein said shaft is operatively connected to said carrier to move said carrier in a first motion, and wherein said carrier is capable of moving in a second motion when subjected to user forces, said head further comprising a spring in operative communication with said carrier, wherein said spring biases insubstantially said carrier when said carrier moves in said first motion and biases said carrier when said carrier moves in said second motion, and wherein said spring's bias upon said carrier is greater during said second motion than said first motion, and wherein said first motion is generally transverse to said longitudinal axis of said head.

17. The electric toothbrush of claim 16, wherein said carrier supports an attachable/detachable bristle plate or an attachable/detachable flossing plate.

18. The electric toothbrush of claim 17, wherein said head comprises a second carrier which oscillates about an axis transverse to said longitudinal axis of said head.

19. The electric toothbrush of claim 16, wherein said bristle plate comprises at least one bristle tuft that forms an acute angle with a top surface of said bristle plate.

20. The electric toothbrush of claim 17, wherein said second carrier comprises an elastomeric finger.

21. The electric toothbrush of claim 16, wherein said head comprises a second carrier that oscillates about an axis transverse to said longitudinal axis of said head.

22. The electric toothbrush of claim 16, wherein said second motion is generally along said longitudinal axis of said head.

23. The electric toothbrush of claim 16, wherein said spring is a spring clip.

* * * * *

UNITED STATES PATENT AND TRADEMARK OFFICE
CERTIFICATE OF CORRECTION

Page 1 of 1

PATENT NO. : 7,861,348 B2
APPLICATION NO. : 11/295907
DATED : January 4, 2011
INVENTOR(S) : John Geoffrey Chan It is certified that error appears in the above-identified patent and that said Letters Patent is hereby corrected as shown below:

On the Title Page

Item (74) Attorney, Agent, or Firm – Please delete "Vlad Witenberg" and insert -- Vlad Vitenberg --.

Signed and Sealed this
Fifteenth Day of March, 2011

David J. Kappos
*Director of the United States Patent and Trademark Office*